(12) United States Patent
Jones, Jr. et al.

(10) Patent No.: US 6,428,314 B1
(45) Date of Patent: Aug. 6, 2002

(54) CONVERTIBLE BUCCAL TUBE

(75) Inventors: J. Hollis Jones, Jr., Conifer; George Kantor, Denver; Michael D. Stevens, Littleton; David E. Watt, Lafayette, all of CO (US)

(73) Assignee: RMO, Inc., Denver, CO (US)

( * ) Notice: Subject to any disclaimer, the term of this patent is extended or adjusted under 35 U.S.C. 154(b) by 0 days.

(21) Appl. No.: 09/839,824

(22) Filed: Apr. 20, 2001

(51) Int. Cl.[7] .................................................. A61C 3/00
(52) U.S. Cl. .............................................. 433/17; 433/8
(58) Field of Search ................... 433/17, 8, 9

(56) References Cited

U.S. PATENT DOCUMENTS

| | | | |
|---|---|---|---|
| 3,391,461 A | 7/1968 | Johnson | 433/17 |
| 3,838,514 A | 10/1974 | Polak | 433/17 |
| 4,134,208 A | 1/1979 | Pearlman | 433/8 |
| 4,498,867 A | 2/1985 | Kesling | 433/16 |
| 4,529,382 A | 7/1985 | Creekmore | 433/9 |
| 4,781,582 A | 11/1988 | Kesling | 433/17 |
| 4,820,151 A | 4/1989 | Pospisil | 433/17 |
| 4,927,362 A * | 5/1990 | Snead | 433/17 |
| 5,059,119 A * | 10/1991 | Snead | 433/17 |
| 5,151,028 A * | 9/1992 | Snead | 433/17 |

FOREIGN PATENT DOCUMENTS

| | | |
|---|---|---|
| DE | 89 03 611 | 7/1990 |
| EP | 0 317 098 A2 | 5/1989 |
| EP | 0 397 533 A2 | 11/1990 |

* cited by examiner

*Primary Examiner*—John J. Wilson
(74) *Attorney, Agent, or Firm*—Sheridan Ross P.C.

(57) ABSTRACT

A convertible buccal tube which includes a base and a body extending from the base. The body includes an elongated first archwire slot and a cover plate extending across and enclosing a buccal side of the first archwire slot. The cover plate is integrally formed with the body. and includes perforated longitudinal connections which form two lines of weaknesses adjacent to the side walls of the archwire slot. The cover plate can be removed to convert the buccal tube to an edgewise bracket.

12 Claims, 4 Drawing Sheets

CONVERTIBLE BUCCAL TUBE

FIELD OF THE INVENTION

The present invention is directed to an orthodontic bracket, and in particular, a convertible buccal tube.

BACKGROUND OF THE INVENTION

A convertible buccal tube is an appliance used by orthodontists during an early phase of treatment to correct malpositioned teeth. The tube is essentially an orthodontic bracket in which the buccal or cheek-facing side of the usual archwire slot is closed by a plate to form a tubular opening of typically rectangular cross section. The plate can be brazed or spot-welded in place. Alternatively, the bracket body can have an integrally formed cover plate with lines of weakness formed by elongated frangible webs extending along the length of the archwire slot, as disclosed in U.S. Pat. No. 4,927,362. In this way, the plate can be removed to convert the buccal tube to a conventional bracket during later stages of treatment.

Convertible buccal tubes have been in use for many years, and reference is made to U.S. Pat. No. 3,391,461 for further background information. Tubes of this type are normally used on younger children whose second molars have not yet grown in, but who have erupted first molars which serve as anchor teeth for an orthodontic archwire. The covered archwire slot provides a terminal buccal-tube anchorage for the archwire during early treatment.

When the second molars erupt, these newly emerged teeth are provided with banded brackets which take over the "anchor" function and receive the terminal ends of a longer archwire. Prior to installation of the longer archwire, the archwire cover plate on each first-molar tube is removed to convert the tube to a conventional molar bracket, and thus to enable normal edgewise treatment of the first molars.

In known convertible buccal tubes of two-piece construction (bracket and cover plate), production expense is increased by the necessary welding, brazing or other attachment process for securing the plate to the appliance body. These known units also sometimes present cover plate removal problems in that the plate may be awkward and difficult to sever from the underlying body.

In the known design of U.S. Pat. No. 4,927,362, production is complicated by the requirement for an extremely precise frangible web thickness. If the web is too thin, it can fracture prematurely; if too thick, it can be difficult to remove the cover. And if the two separate webs are of different thicknesses, the plate might only shear along one of the webs; thereafter, the orthodontist would have to use an awkward back-and-forth twisting motion in an arc perpendicular to the remaining connected web to achieve fatigue and eventual fracture the web.

It would be desirable to have a convertible buccal tube design which is easy to manufacture. It would be desirable to have a convertible buccal tube design in which the cover plate is integrally formed with the bracket body. It would be desirable to have a convertible buccal tube design in which the areas of weakness provided for the removal of the cover could be easily and reproducibly manufactured. It would be desirable to have a convertible buccal tube design in which the cover plate has an essentially rectangular shape with little or no variation in thickness.

SUMMARY OF THE INVENTION

The convertible buccal tube of this invention is an integrally molded, cast, sintered or machined product comprising an orthodontic bracket with a body defining an archwire slot which is covered on the buccal side by an integral cap or plate. The occlusal and gingival sides of the plate are joined to the bracket by integral portions of perforated material forming potential fracture lines which break away when the plate is removed. Preferably the thickness of the cover plate is substantially uniform, with the exceptions of the perforations which have no thickness.

One embodiment of the present invention is directed to a convertible buccal tube having a base designed for direct or indirect attachment of a tooth, a body extending from the base and defining an elongated first archwire slot, and a cover plate extending across and closing a buccal side of said first archwire slot, such plate being integrally joined to the body adjacent opposite sides of the slot by perforated longitudinal connections forming two lines of weakness, whereby the plate can be removed from the body along body of the perforated lines of weakness to open the slot. The perforated longitudinal connections forming two lines of weakness preferably comprise metal alternating with holes formed in the metal. The metal is preferably substantially of the same thickness as the cover plate and the perforations are preferably oblong slots extending through the cover plate. The oblong slots are preferably from about 10–12 mm by about 25–40 mm and the thickness of the cover plate is from about 3–5 mm up to 15–20 mm, even more preferably between about 12.5–15 mm. In other embodiments, a second archwire slot is provided parallel to a first archwire slot, such second archwire slot preferably covered by a plate which is not designed to be removed. The present invention can further comprise an auxiliary tube, preferably positioned parallel to and offset from a first archwire slot.

Other embodiments within the scope of the present invention will be clear to those of skill in the art after a review of the detailed description of the invention and the accompanying drawings.

DETAILED DESCRIPTION OF THE INVENTION

Figure 1:
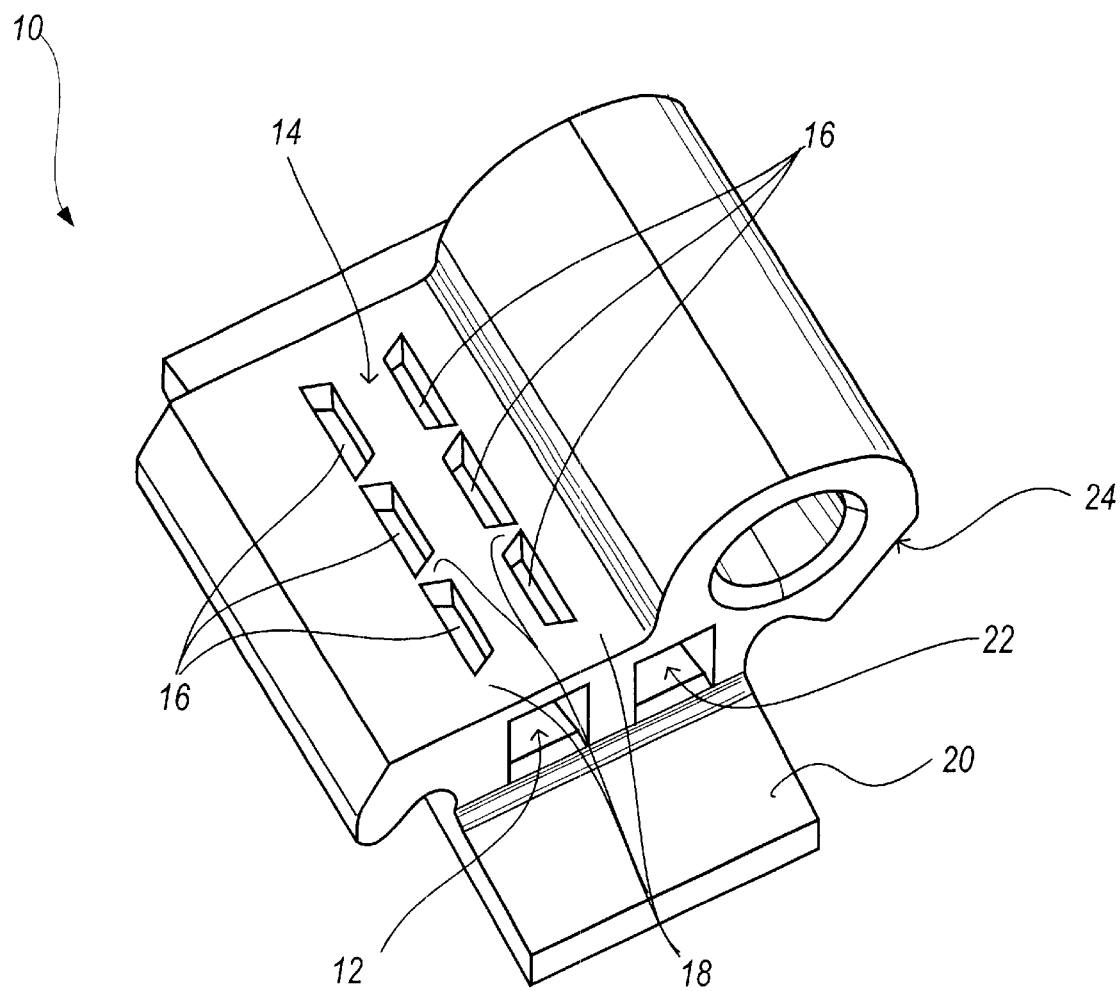
FIG. 1 illustrates a top perspective view of a convertible buccal tube in accordance with the present invention, with the cover plate in place.

In accordance with the present invention, a convertible buccal tube 10 is provided. As illustrated in FIG. 1, the convertible buccal tube 10 includes a first archwire slot 12 which is covered by a cover plate 14. Extending along the two outer edges of the cover plate 14 are two perforated longitudinal connections forming a line of weakness. Preferably, the perforations 16 are longer in the mesiodistal direction than they are wide in the occlusogingival direction, however, all sizes and shapes of apertures can be used to address specific manufacturing and/or use requirements, without departing from the scope of the present invention. Between the perforations 16 are connecting portions 18. Preferably, the connecting portions 18 are integrally formed with and made of the same material as the cover plate 14 and have substantially the same thickness as the cover plate 14.

The convertible buccal tube 10 includes a base 20 that can be employed in connecting the convertible buccal tube 10 to a patient's tooth. Any suitable means of attachment, whether presently known or developed in the future, can be used to attach the convertible buccal tube 10 to the patient's tooth (not shown). Various methods for attaching the bracket to the tooth may be employed, including direct bonding to a tooth, welding flanges onto a band which is then connected to a tooth, via a mesh base, etc.

In one embodiment of the present invention, a second archwire slot 22 is provided. Preferably, the second archwire slot 22 does not include a removable cover plate. Preferably, an auxiliary tube 24 is included with the convertible buccal tube 10. Preferably, the auxiliary tube 24 is parallel to and offset from the first archwire slot 12. The purpose of the second archwire slot is to facilitate an auxiliary secondary archwire, and/or a headgear tube, auxiliary appliances, and for potentially different phases of treatment.

Figure 2:
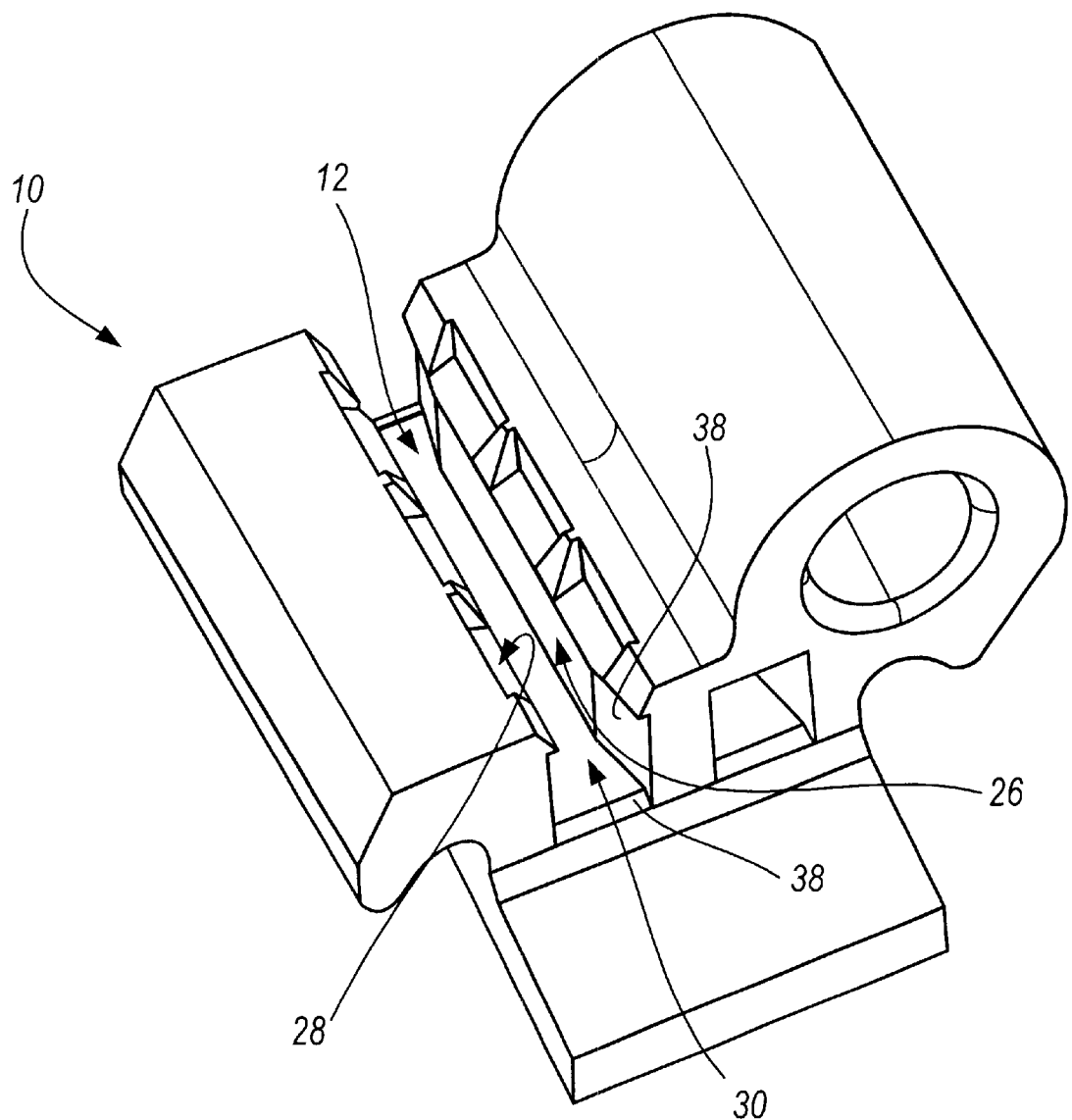
FIG. 2 illustrates a top perspective view of the convertible buccal tube of FIG. 1, with the cover plate removed.

In FIG. 2, the convertible buccal tube 10 of FIG. 1 is illustrated, however, the cover plate 14 (not shown) has been removed. With the cover plate 14 removed, the interior of the archwire slot 12 can be seen. The archwire slot 12 includes a floor 30, a first side wall 26 and a second side wall 28. When the cover plate 14 is removed, the convertible buccal tube can be used as an edgewise bracket. The archwire slot 12 can be configured to have relief protrusions on the sidewalls and archwire slot floor.

Figure 3:
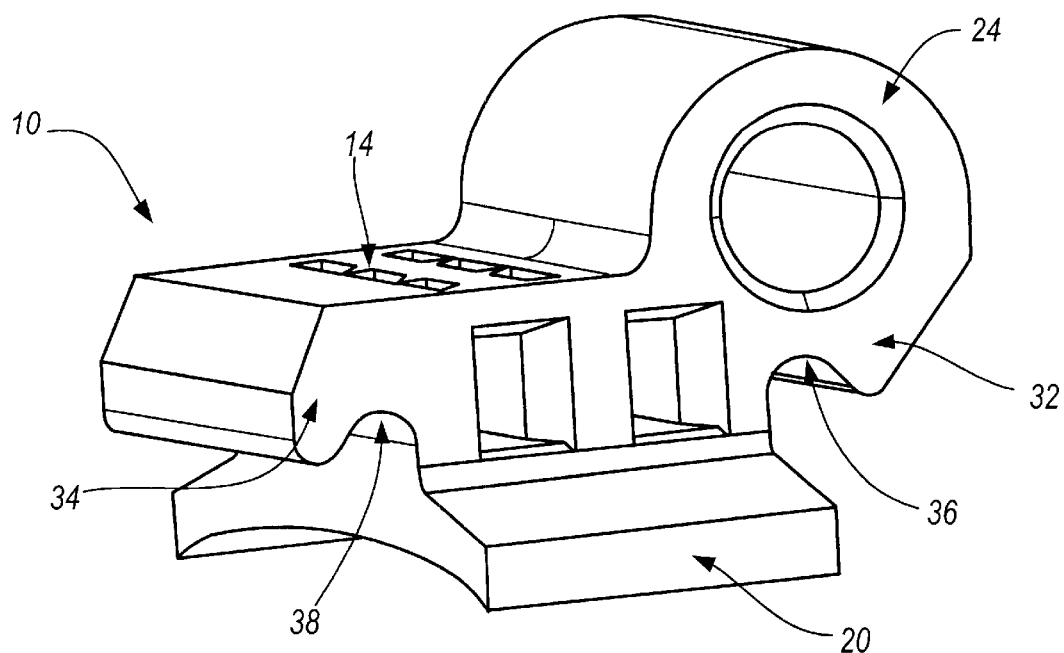
FIG. 3 illustrates a front plan view of the convertible buccal tube of FIG. 1

After the cover plate 14 has been removed, it is useful to employ one or more ligatures to maintain the archwire (not shown) within the first archwire slot 12. As illustrated in FIG. 3 (which shows cover plate 14 still in place), a first tie wing 32 is formed from the lower portion of the auxiliary tube 24. A second tie wing 34 is also shown. The under portions of the first and second tie wings 32, 34 form first and second ligature grooves 36, 38. Ligatures (not shown) can be wrapped under the ligature grooves 36,38 and over the top of the archwire (not shown) in order to keep the archwire in place.

Figure 5:
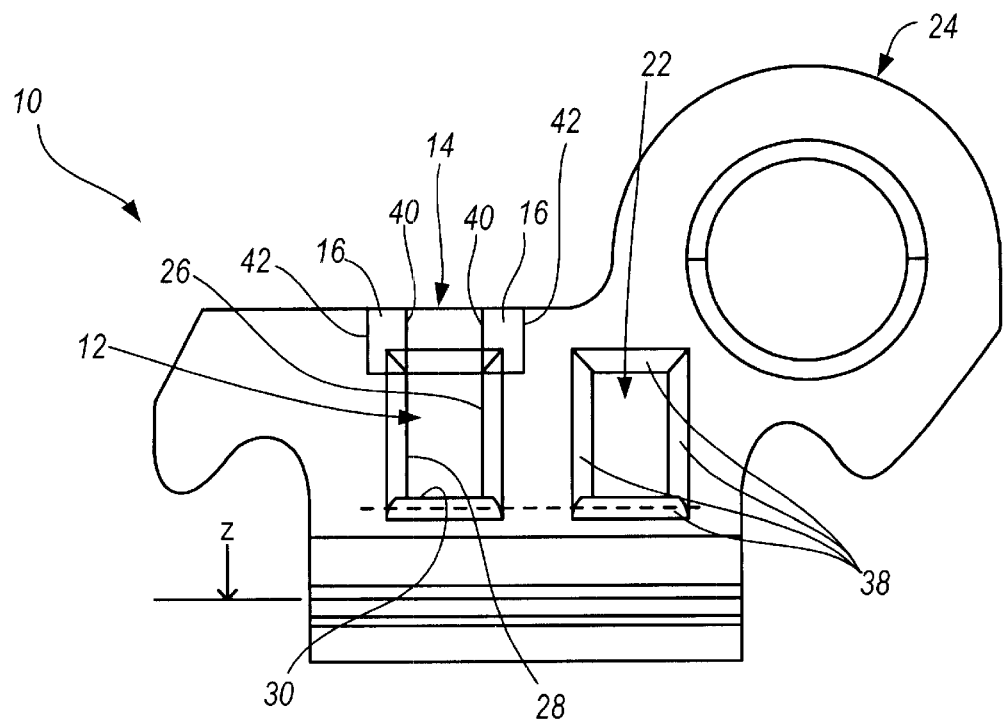
FIG. 5 illustrates a front plan view of the convertible buccal tube of FIG. 1.
Figure 4:
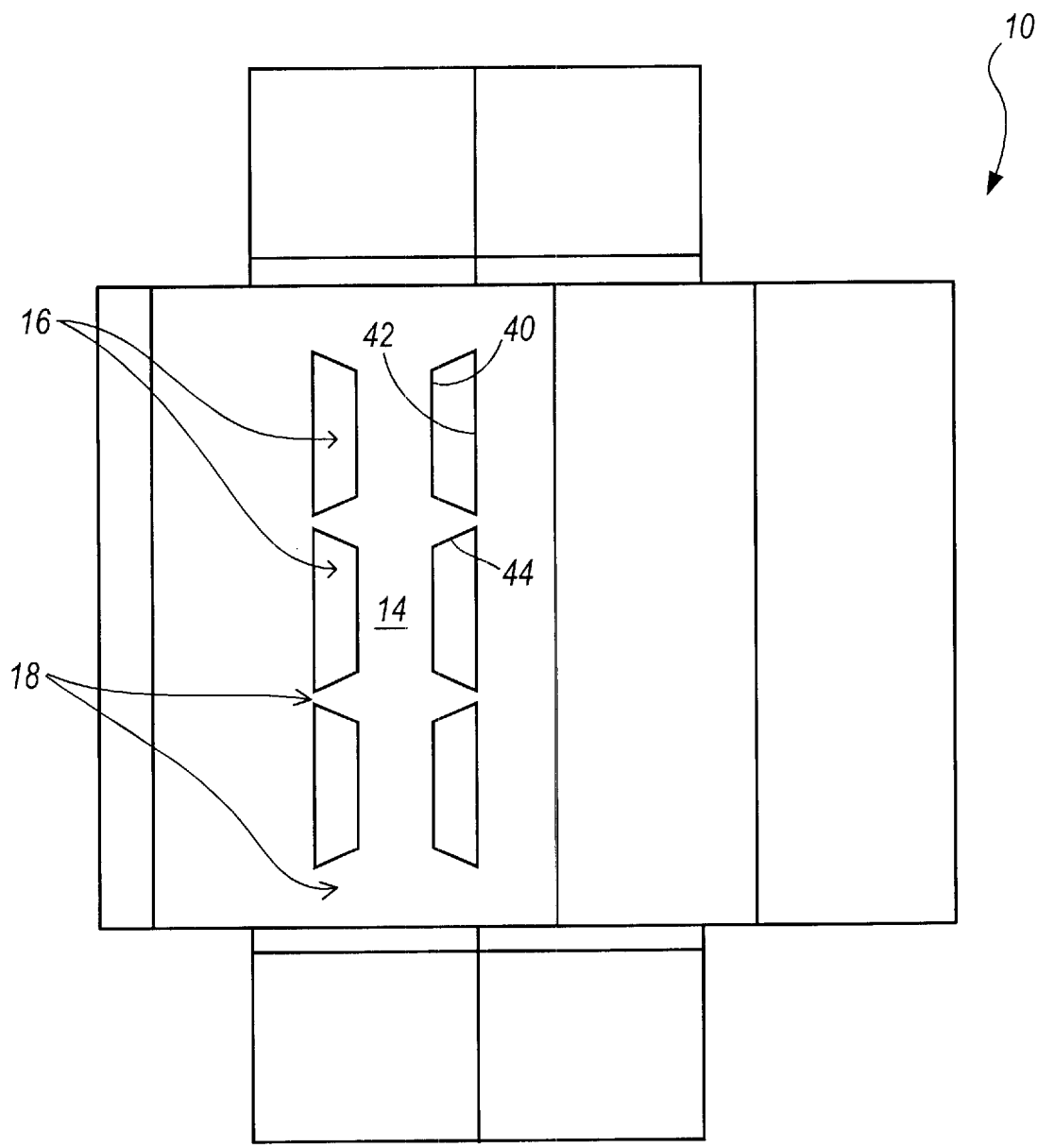
FIG. 4 illustrates a top plan view of the convertible buccal tube of FIG. 1.

As illustrated in FIG. 4, the perforations 16 are preferably longer than the connecting metal 18 therebetween. This aids in the separation of the cover plate 14 from the convertible buccal tube 10. The perforations are preferably elongated slots 16. The number and dimension of apertures forming the perforations can be varied, however, preferably there are more perforations along a straight line than there is material between such apertures along the same line. The perforations 16 are preferably between about 25–40 mm, and more preferably about 12.5–15 mm, have a width of preferably 3–10 mm, and more preferably 3–5 mm. Preferably, one or more of the elongated slots 16 are trapezoidal in shape, with the longest parallel side 42 along the outer edge of the cover plate 14, the shorter parallel edge 40 towards the center of the cover plate 14, and the two shortest nonparallel edges 44 at the mesiodistal ends of the elongated slot 16. As illustrated in FIG. 5, the inner sides 40 of the perforations 16 (shown in phantom) are substantially coextensive with the first and second side walls 26, 28 and the outer sides 42 of the perforations 16 (shown in phantom) are located outside, beyond the first and second side walls 26, 28.

As illustrated in FIG. 5, chamfered openings 38 can be provided in one or both entrances to one or both of the archwire slots 12, 22. In this way, the initial entrance to the archwire slots 12, 22 is wider, allowing for easier threading of the archwire (not shown) through the archwire slots 12, 22. Because the entrance to the archwire slots 12, 22 is larger than the archwire, easier threading of the archwire through the bracket 10 is provided, in much the same manner that a countersink simplifies the placement of a screw in a pre-drilled hole.

Preferably, the convertible buccal tube is manufactured by molding and sintering, however, the apertures can alternatively be formed by laser techniques, etc.

In use, the base 20 of the buccal tube 10 is typically secured to a tooth band (not shown) which is in turn cemented to a first molar tooth. Direct-bonding techniques may also be used, though banded attachment is normally preferred on these posterior teeth. A terminal end of a conventional archwire is then fitted into the tube 10 for early-stage orthodontic treatment. After the patient's second molars erupt sufficiently, these teeth are banded with buccal tubes to serve as the terminal anchoring teeth in the dental arch. The initial archwire is removed, and the cover plates 14 are removed from buccal tubes 10 on the first molars to convert these tubes 10 to edgewise brackets with buccally open archwire slots 12. A technique for cover plate 14 removal involves use of a prying tool inserted in the archwire slot 12 which is manipulated to shear the plate 14 away from the underlying body. As one of skill in the art will appreciate, there are various other ways in which to remove the cover plate 14 from the buccal tube, including use of different metals, plastics, ceramics, polymers, etc., which have distinct physical characteristics that would allow for the separation of the cover from the rest of the device. Indeed, alternative methods to remove a cover 14 include the provision of drawstring-like structures which, when pulled, will separate one edge of the cover 14 from the rest of the device. Still other techniques that may be employed include chemical dissolution of particular portions of the cover to permit easy removal, laser techniques to separate the cover from the rest of the device, etc. All of the above methods and techniques are well within the scope of the present invention as hereinabove described.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A convertible buccal tube, comprising:
   a. a base designed for direct or indirect attachment to a tooth;
   b. a body extending from the base, and defining an elongated first archwire slot; and
   c. a cover plate extending across and closing a buccal side of said first archwire slot, said plate being integrally joined to the body adjacent opposite sides of the slot by perforated longitudinal connections forming two lines of weakness, whereby the plate can be removed from the body along both of the perforated lines of weakness to open the slot, wherein said perforated longitudinal connections forming two lines of weakness comprise metal alternating with holes formed in said metal, said metal is substantially of the same thickness as said cover plate.

2. A convertible buccal tube, comprising:
   (a) a base designed for direct or indirect attachment to a tooth;
   (b) a body extending from the base, and defining parallel elongated first and second archwire slots; and (c) a cover plate extending across and closing a buccal side of said first archwire slot, said plate being integrally joined to the body adjacent opposite sides of the slot by perforated longitudinal connections forming two lines of weakness, wherein at least one perforation is a trapezoidal slot extending through said the cover plate, whereby the plate can be removed from the body along both of the perforated lines of weakness to open the slot and wherein the thickness of the cover plate is substantially uniform in thickness and is from about 0.5 to about 1 mm thick.

3. The convertible buccal tube of claim 2 wherein said trapezoidal slot is from about 3 to about 10 mm wide and from about 25 to about 40 mm long.

4. The convertible buccal tube of claim 2 wherein said second archwire slot is covered by a plate which is not designed to be removed.

5. The convertible buccal tube of claim 2 further comprising an auxiliary tube.

6. The convertible buccal tube of claim 5 wherein said auxiliary tube is parallel to and offset from said first archwire slot.

7. The convertible buccal tube of claim 2, further comprising a chamfered entrance opening to at least one of said archwire slots to aid in the insertion of the archwire.

8. The process for converting a buccal tube to an edgewise bracket, comprising:

a. providing a base designed for direct or indirect attachment to a tooth;

b. providing a body extending from the base, and defining parallel elongated first and second archwire slots;

c. providing a cover plate extending across and closing a buccal side of said first archwire slot, said plate being integrally joined to the body adjacent opposite sides of the slot by perforated longitudinal connections forming two lines of weakness, wherein at least one perforation is a trapezoidal slot extending through said the cover plate, whereby the plate can be removed from the body along both of the perforated lines of weakness to open the slot and wherein the thickness of the cover plate is substantially uniform in thickness and is from about 0.5 to about 1 mm thick; and d. removing said cover plate.

9. The process of claim 8 wherein said perforated longitudinal connections forming two lines of weakness comprise metal alternating with holes formed in said metal.

10. The process of claim 9, wherein said metal is substantially of the same thickness as said cover plate.

11. The process of claim 8 wherein said perforated longitudinal connections forming two lines of weakness comprise metal alternating with trapezoidal slots.

12. The process of claim 8 wherein said oblong slots are from about 3 to about 10 mm wide and from about 25 to about 40 mm long.

* * * * *